United States Patent [19]

Chang et al.

[11] Patent Number: 5,382,731

[45] Date of Patent: Jan. 17, 1995

[54] COMBINED PARAFFIN ISOMERIZATION/RING OPENING PROCESS

[75] Inventors: Clarence D. Chang, Princeton, N.J.; Roy D. Bastian, Bethlehem, Pa.; Scott Han, Lawrenceville, N.J.; Jose G. Santiesteban, Yardley, Pa.

[73] Assignee: Mobil Oil Corp., Fairfax, Va.

[21] Appl. No.: 95,885

[22] Filed: Jul. 22, 1993

[51] Int. Cl.⁶ .................... C07C 1/00; C07C 5/13
[52] U.S. Cl. .................... 585/315; 585/310; 585/700; 585/737; 585/738; 585/748; 585/750; 585/940
[58] Field of Search ............... 585/310, 315, 700, 737, 585/738, 748, 750, 940

[56] References Cited

U.S. PATENT DOCUMENTS

| | | | |
|---|---|---|---|
| 3,617,511 | 11/1971 | Jenkins et al. | 208/112 |
| 4,783,575 | 11/1988 | Schmidt et al. | 585/748 |
| 4,918,041 | 4/1990 | Hollstein et al. | 502/217 |
| 5,113,034 | 5/1992 | Soled et al. | 585/510 |

FOREIGN PATENT DOCUMENTS

1288339 11/1989 Japan .

OTHER PUBLICATIONS

Hino, M. et al., "Synthesis of Solid Superacid of Tungsten Oxide Supported Zirconia and its Catalytic Action for Reactions of Butane and Pentane," J. Chem. Soc., Chem. Commun., 1259–1260 (1988).

Proceedings 9th Intern. Congress on Catalysis, vol. 4, Oxide Catalysts and Catalyst Development, M. J. Phillips et al, ed., 1727–1734 (1988).

*Primary Examiner*—Helen M. S. Sneed
*Assistant Examiner*—Nhat D. Phan
*Attorney, Agent, or Firm*—Alexander J. McKillop; Dennis P. Santini; Edward F. Kenehan, Jr.

[57] ABSTRACT

There is provided a process for ring opening of aromatics or cycloaliphatics, as well as isomerization of aliphatics. The feedstream to this process comprises hydrocarbons having 6 carbon atoms. The process involves the use of a recycle stream containing a source of chlorine, such as carbon tetrachloride, and this process involves the use of at least two reactors connected in series. The first reactor comprises a ring opening catalyst and is operated under conditions which particularly promote ring opening. The catalyst in this first reactor may comprise zirconia modified with tungstate and platinum. A second, downstream reactor is operated under conditions to promote isomerization of aliphatics. The catalyst in the second reactor may comprise alumina, platinum and a chloride component. The catalysts in both the first and second reactors are chlorine resistant.

15 Claims, 2 Drawing Sheets

COMBINED PARAFFIN ISOMERIZATION/RING OPENING PROCESS

BACKGROUND

There is provided a process for ring opening of aromatics or cycloaliphatics, as well as isomerization of aliphatics. The feedstream to this process comprises $C_6$ cycloparaffins and/or benzene. The process involves the use of a recycle stream containing a source of chlorine, and this process involves the use of at least two reactors connected in series. The first reactor comprises a ring opening catalyst and is operated under conditions which particularly promote ring opening. A second, downstream reactor is operated under conditions to promote isomerization of aliphatics. The catalysts in both of the first and second reactors are chlorine resistant.

A unit process which is frequently encountered in petroleum refining is paraffin isomerization. Paraffin isomerization of linear (straight chain) paraffins produces branched chain paraffins. In such a process, as conventionally operated, low molecular weight $C_4$-$C_6$ paraffins are converted to iso-paraffins in the presence of an acidic catalyst such as aluminum chloride. Recently, $C_6+$, preferably $C_{10}+$ n-paraffins, have been isomerized, in the presence of large pore size zeolites to produce branched chain paraffins by skeletal rearrangement. The latter process can find application in dewaxing.

Isomerization is one of several reactions which occur in reforming of naphthas. Reforming of naphthas is undertaken to upgrade a low octane naphtha to a higher octane effluent. One of the octane enhancing reactions which occurs during reforming is the isomerization of n-paraffins to isoparaffins. Under the process conditions of reforming, other reactions which occur are aromatization (or dehydrocyclization), and dehydrogenation, with some cracking.

Paraffin isomerization catalysts may also be employed as ring opening catalysts for removal of aromatics and aromatic precursors from reformer feedstocks. For example, cyclohexane, a precursor to benzene, may be rearranged over a paraffin isomerization catalyst to a mixture of branched paraffins. Branched paraffins are only partly aromatized in reforming whereas cyclohexane is almost completely converted to benzene. Application of paraffin isomerization catalysts for ring opening aromatics and aromatic precursors will no doubt become more important as environmental regulations limiting aromatics in gasoline become more stringent.

SUMMARY

There is provided a process for ring opening and isomerization of hydrocarbons, said process comprising the steps of:
 (a) charging hydrocarbons comprising $C_6$ cyclic hydrocarbons along with a source of chlorine and hydrogen to a first reaction zone, wherein said hydrocarbons, said source of chlorine and hydrogen are contacted with a ring opening catalyst under conditions sufficient to saturate benzene and open cyclic hydrocarbons contained in said hydrocarbons, wherein said catalyst comprises (i) a hydrogenation/dehydrogenation component and (ii) an acidic solid component comprising a Group IVB metal oxide modified with an oxyanion of a Group VIB metal; and
 (b) charging the hydrocarbon product from said first reaction zone along with a source of chlorine and hydrogen to a second reaction zone, wherein hydrocarbons and hydrogen are contacted with an isomerization catalyst under conditions sufficient to isomerize paraffins.

There is also provided a process for ring opening and isomerization of hydrocarbons, said process comprising the steps of:
 (a) passing hydrocarbons comprising $C_6$ cyclic hydrocarbons and a hydrocarbon recycle stream comprising a source of chlorine to a fractionation zone;
 (b) withdrawing a sidecut comprising $C_6$ hydrocarbons and a majority of the $C_6$ cyclic hydrocarbons entering said fractionation zone;
 (c) charging said sidecut along with hydrogen and a source of chlorine to a first reaction zone, wherein said sidecut and hydrogen are contacted with a ring opening catalyst under conditions sufficient to saturate benzene and open cyclic hydrocarbons contained in the sidecut, wherein said catalyst comprises (i) a hydrogenation/dehydrogenation component and (ii) an acidic solid component comprising a Group IVB metal oxide modified with an oxyanion of a Group VIB metal;
 (d) charging the hydrocarbon product from said first reaction zone along with a source of chlorine and hydrogen to a second reaction zone, wherein hydrocarbons and hydrogen are contacted with an isomerization catalyst under conditions sufficient to isomerize paraffins;
 (e) recovering an effluent from said second reaction zone and returning said effluent to said fractionation zone as said hydrocarbon recycle stream;
 (f) recovering a second stream from said fractionation zone comprising $C_7$ hydrocarbons; and
 (g) recovering a third stream from said fractionation zone comprising 2,2-dimethylbutane and lower boiling hydrocarbons.

There is also provided a process for ring opening and isomerization of hydrocarbons, said process comprising the steps of:
 (a) passing hydrocarbons comprising $C_6$ cyclic hydrocarbons and a hydrocarbon recycle stream to a fractionation zone;
 (b) withdrawing a sidecut comprising $C_6$ hydrocarbons and a majority of the $C_6$ cyclic hydrocarbons entering said fractionation zone;
 (c) charging said sidecut along with hydrogen and a source of chlorine to a first reaction zone, wherein said sidecut and hydrogen are contacted with a ring opening catalyst under conditions sufficient to open cyclic hydrocarbons contained in the sidecut, wherein said catalyst comprises (i) a hydrogenation/dehydrogenation component and (ii) an acidic solid component comprising a Group IVB metal oxide modified with an oxyanion of a Group VIB metal;
 (d) removing hydrogen from the effluent of the first reaction zone under conditions so that the effluent has a hydrogen to hydrocarbon mole ratio of less than 0.05;
 (e) recycling hydrogen removed in accordance with step (d) to said first reaction zone;

(f) charging the effluent from said first reaction zone having a hydrogen to hydrocarbon mole ratio of less than 0.05 to a second reaction zone, wherein hydrocarbons, a source of chlorine, and hydrogen are contacted with an isomerization catalyst under conditions sufficient to isomerize paraffins;

(g) recovering an effluent from the second reaction zone and returning said effluent from the second reaction zone to said fractionation zone as said hydrocarbon recycle stream;

(h) recovering a second stream from said fractionation zone comprising $C_7$ hydrocarbons; and (i) recovering a third stream from said fractionation zone comprising 2,2-dimethylbutane and lower boiling hydrocarbons.

EMBODIMENTS

Figure 1:
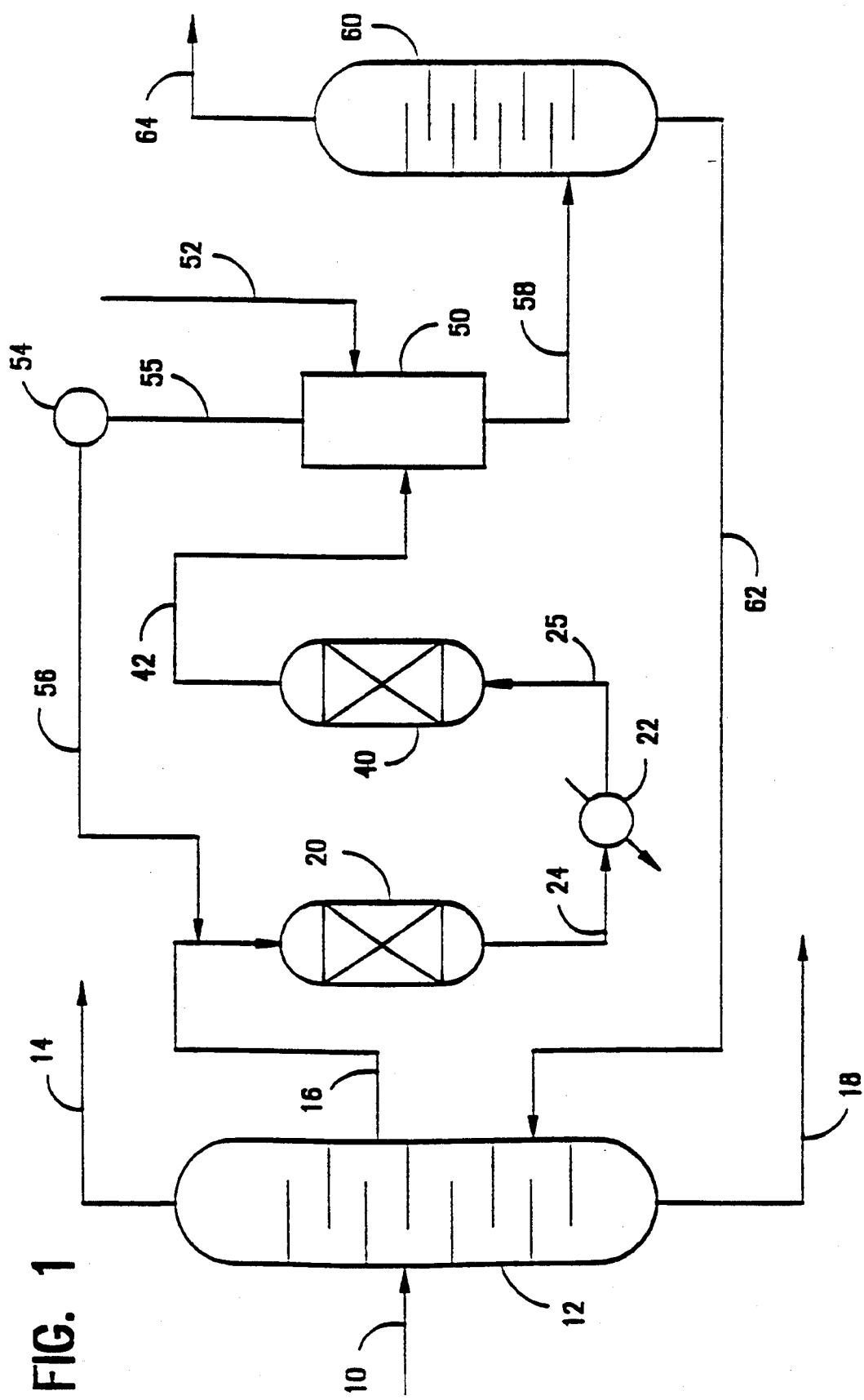
FIGS. 1 and 2 provide schematic representations of embodiments of the present process.

The catalytic ring opening/isomerization process described herein is operated to ring open $C_6$ cyclic hydrocarbons and isomerize the acyclic products together with n-paraffins and mono-methyl branched paraffins to produce a high octane stream.

In the present ring opening/isomerization process n-paraffinic and mono-methyl branched paraffinic components are isomerized to higher branched paraffins which are generally better octane boosters. By way of illustration, the significance of these reactions can be gleaned from a review of the following table of Octane Numbers of Pure Hydrocarbons from P. H. Emmett, ed., *Catalysis*, vol. VI (1958).

Octane Numbers of Pure Hydrocarbons

| Hydrocarbon | Blending Research Octane Number (clear) |
|---|---|
| Paraffins: | |
| n-heptane | 0 |
| 2-methylhexane | 41 |
| 3-methylhexane | 56 |
| 2,2-dimethylpentane | 89 |
| 2,3-dimethylpentane | 87 |
| 2,2,3-trimethylbutane | 113 |

The feedstock for the present process is one which contains significant amounts of $C_5+$ normal and/or slightly branched paraffins. In addition, the feedstock contains monocyclic aromatic compounds and/or cyclic paraffins, such as cyclohexane. Among the hydrocarbons having 6 or less carbon atoms in the feedstock, at least 1 wt. %, e.g. at least 5 wt. %, e.g. at least 10 wt. %, e.g. at least 20 wt. %, e.g. at least 30 wt. %, of these hydrocarbons may be cyclic hydrocarbons, e.g. aromatics or cyclic paraffins.

The ring opening catalyst in the first reaction zone described herein comprises an oxide of a Group IVB metal, preferably zirconia or titania. This Group IVB metal oxide is modified in two ways. According to one modification, the Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, Volume 4, pages 1727–1735 (1988), the entire disclosures of these publications are expressly incorporated herein by reference.

According to another modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst preferably comprises one or more catalytic forms of one or more noble metals (i.e., Pt, Pd, Ir, Rh, Os or Ru). Combinations of catalytic forms of such noble or non-noble metals, such combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, Volume 4, pages 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present ring opening catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

Suitable sources of the Group IVB metal oxide, used for preparing the present ring opening catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium i-propoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr—O—Zr, further comprising available surface hydroxy groups. These available surface hydroxyl groups are believed to react with the source of an anion of a Group IVB metal, such as tungsten, to form the present acidic catalyst component. As suggested in the aforementioned article by K. Arata and M. Hino in *Proceedings 9th International Congress on Catalysis*, Volume 4, pages 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, as demonstrated in Examples recited hereinafter, especially in Examples 5–14, refluxing hydrated zirconia in an $NH_4OH$ solution having a pH of greater than 7 was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The hydrogenation/dehydrogenation component of the present ring opening catalyst may be derived from Group VIII metals, such as platinum, iridium, osmium, palladium, rhodium, ruthenium, nickel, cobalt, iron and mixtures of two or more thereof. These components may optionally be mixed with components derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride.

The present ring opening catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The hydrogenation/dehydrogenation component of the catalyst (e.g., Group VIII metal, Group VIIB metal, etc.) may be added after or before the calcination step by techniques known in the art, such as impregnation, coimpregnation, coprecipitation, physical admixture, etc. The hydrogenation/dehydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperature may not be needed.

In the present ring opening catalyst, of the Group IVB oxides, zirconium oxide is preferred; of the Group VIB anions, tungstate is preferred; and of the hydrogenation/dehydrogenation components, platinum and/or platinum-tin are preferred.

Qualitatively speaking, elemental analysis of the present ring opening catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present ring opening catalyst, it is best not to be restricted by any particular quantities of oxygen. In functional terms, the amount of Group VIB oxyanion in the present ring opening catalyst may be expressed as that amount which increases the acidity of the Group IVB oxide. This amount is referred to herein as an acidity increasing amount. Elemental analysis of the present ring opening catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form $YO_3$. It will be appreciated, however, that these forms of oxides, i.e., $XO_2$ and $YO_3$, may not actually exist, and are referred to herein simply for the purposes of calculating relative quantities of X and Y in the present ring opening catalyst. The present ring opening catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present ring opening catalyst may comprise, for example, from about 0.001 to about 5 wt %, e.g., from about 0.1 to about 2 wt %, of the hydrogenation/dehydrogenation component, especially when this component is a noble metal.

The acidic solid of the ring opening catalyst can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the acidic solid can be extruded before drying or partially dried and then extruded.

It may be desired to incorporate the acidic solid of the ring opening catalyst with another material which is resistant to the temperatures and other conditions employed in the present process. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the catalyst, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the acidic solid of the ring opening catalyst include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the acidic solid can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided acidic solid and inorganic oxide matrix vary widely, with the acidic solid content ranging from about 1 to about 90 percent by weight and more usually, particularly when the composite is prepared in the form of beads, in the range of about 2 to about 80 weight percent of the composite.

In the first reaction zone, the temperature should be high enough to promote substantial ring opening without causing excessive cracking of hydrocarbons to $C_4$-hydrocarbons. This reaction temperature may be at least 150° C. e.g. from 230° C. to 270° C. Pressures may range from atmospheric up to 1000 psig. The preferred range is from 50 to 500 psig. Weight hourly space velocity is generally from 0.1 to 50 $hr^{-1}$, more usually 0.2 to 10 $hr^{-1}$. The hydrogen:hydrocarbon molar ratio in the charge stock to the first reaction zone is generally from 0.1:1 to 10:1.

The reaction conditions in the first reaction zone may be sufficient to cause at least 10 wt. %, e.g. at least 25 wt. %, e.g. at least 50 wt %, of the cyclic hydrocarbons introduced into this zone to undergo ring opening.

The reaction conditions in the second reaction zone may be milder, particularly in terms of lower temperature conditions, to optimize isomerization of paraffins to higher octane value isomers. The theoretical equilibrium concentration of high octane isomers, such as 2,2-dimethylbutane, increases with lower temperature conditions. Thus, high yields of desirable high octane isomers are achievable at lower temperature conditions.

In order to use lower temperatures in the second reaction zone, it is preferred to use a catalyst which is highly reactive for isomerization. Examples of such highly reactive catalysts, which may be used in the second reaction zone, include those catalysts described in U.S. Pat. Nos. 4,783,575; 4,804,803; and 4,834,866, the entire disclosures of which are expressly incorporated herein by reference. These catalysts comprise alumina, platinum and a chloride component.

The isomerization catalyst in the second reaction zone may be a high chloride catalyst on an aluminum base containing platinum. The aluminum is preferably an anhydrous gamma-alumina with a high degree of purity. The catalyst may also contain other platinum group metals. The term platinum group metals refers to noble metals excluding silver and gold which selected from the group consisting of platinum, palladium, germanium, ruthenium, rhodium, osmium, and iridium. These metals demonstrate differences in activity and selectivity such that platinum has now been found to be the most suitable for this process. The catalyst may contain at least about 0.1 wt. %, e.g. from about 0.1 to about 1.0 wt. %, e.g. from about 0.1 to 0.25 wt. %, of platinum. Other platinum group metals may be present in a concentration of at least about 0.1 wt. %, e.g. from about 0.1 to 1.0 wt. %, e.g. from 0.1 to 0.25 wt. %. The platinum component may exist within the final catalytic composite as an oxide or halide or as an elemental metal. The presence of the platinum component in its reduced state has been found most suitable for this process.

The catalyst of the second reaction zone may also contain a chloride component. The chloride component termed in the art "a combined chloride" may be present in an amount of at least about 2 wt. %, e.g. from about 2 to about 20 wt. %, e.g. from about 2 to about 10 wt. %, based upon the dry support material. The use of chloride in amounts greater than 5 wt. % are believed to be the most beneficial for this process.

There are a variety of ways for preparing this catalytic composite and incorporating the platinum metal and the chloride therein. One method prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the chloride concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the feedstock contacting this catalyst must be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

It has been recognized that cyclic hydrocarbons, especially $C_6$ cyclics such as benzene, cyclohexane and methylcyclopentane adversely affect the degree of paraffin isomerization over this particular type of alumina/platinum/chloride catalyst. The adverse effect is believed to be caused by preferential adsorption of the cyclic hydrocarbons on the catalyst surface and the resulting exclusion of the paraffinic hydrocarbons. However, the adverse effect is minimized by sustantially removing cyclics in the first reaction zone. Operating conditions within the second reaction zone are selected to maximize the production of isoalkane product from the feed components. Temperatures within the reaction zone will usually range from about 40° C. to 180° C. Lower reaction temperatures are preferred for purposes of isomerization conversion since they favor isoalkanes over normal alkanes in equilibrium mixtures.

The hydrogen to hydrocarbon molar ratio in the second reaction zone may be from 0.01 to 10, e.g. from 0.01 to 5. However, it is noted that the primary reaction, i.e., isomerization, which takes place in this zone, does not consume net hydrogen. Furthermore, the types of side reactions, e.g. saturation of olefins and aromatics, which consume hydrogen, take place primarily in the first reaction zone. Accordingly, the hydrogen to hydrocarbon molar ratio in the second reaction zone may be quite small, e.g. 0.05 or less.

The pressure in the second reaction zone may be maintained over a wide range of pressures. Pressure conditions may range from 50 to 1500 psig. The feed rate to the second reaction zone can also vary over a wide range. These conditions include weight hourly space velocities ranging from 0.1 to 50 hr.$^{-1}$, however, space velocities between 0.5 and 3 hr.$^{-1}$ are preferred.

When the above-mentioned alumina/platinum/chloride catalyst is used, operation of the second reaction zone also requires the presence of a small amount of an organic chloride promoter. The organic chloride promoter serves to maintain a high level of active chloride on the catalyst as small amounts of chloride are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

More than one reactor may be employed in each of the above-mentioned reaction zones. The use of two reactors permits a variation in the operating conditions between the two reactors to enhance cyclic hydrocarbon conversion in the first reactor. In this manner, the first reactor operates at higher temperature and pressure conditions that favor ring opening. The likelihood of exothermic reactions, such as the hydrogenation of unsaturates, occurring in the initial portion of the reaction zone facilitates the use of higher temperatures therein. Once the rings have been opened, the final reactor stage may operate at temperature conditions that are more favorable for isoalkane equilibrium.

Another benefit of using two reactors is that it allows partial replacement of the catalyst system without taking the isomerization unit off stream. For short periods of time, during which the replacement of catalyst may be necessary, the entire flow of reactants may be processed through only one reaction vessel while catalyst is replaced in the other.

After the feedstock has encountered the second reaction zone, the effluent of the process will enter separation facilities in the recovery of an isoalkane product. At minimum, the separation facilities divide the reaction zone effluent into a product stream comprising $C_4$ and heavier hydrocarbons and a gas stream which is made up of lighter hydrocarbons and hydrogen. Suitable designs for rectification columns and separator vessels are well known to those skilled in the art. The separation section may also include facilities for recovery of normal alkanes. Normal alkanes recovered from the separation facilities may be recycled to the isomerization reaction zone to increase the conversion of normal alkanes to isoalkanes. Typical separation facilities will comprise a stabilizer section that receives the effluent from the reaction and includes at least one stabilizer column. The stabilizer column is operated to deliver a bottoms fraction containing $C_4$ and heavier hydrocarbons and an overhead fraction of $C_3$ hydrocarbons and lighter boiling compounds. The heavier hydrocarbons recovered from the bottom of the stabilizer column are cooled and may be further separated into a product stream and a reflux stream. $C_3$ and lighter hydrocarbons taken overhead from the stabilizer column are cooled, condensed and separated into a reflux stream that is returned to the process and a wet gas stream. The wet gas stream enters a scrubber section that contacts the gas with a suitable treatment solution for neutralizing and/or removing acidic components that may have originated with the chloride addition to the isomerization zone and may by present in the gas stream.

FIG. 1 provides a schematic representation of an embodiment of the present process. $C_6+$ naphtha enters through line 10 to distillation column 12. The $C_6+$ naphtha is separated into three fractions: high octane $C_6$ isoparaffins (primarily 2,2-dimethylbutane) which are collected overhead in line 14 and used as a high octane blending component; lower octane $C_6$ paraffins (i.e., 2-methylpentane) and cycloparaffins (i.e., cyclohexane) which are concentrated in line 16; and $C_7+$ hydrocarbons which are sent via line 18 to the reformer.

Low octane $C_6$ paraffins and cycloparaffins are piped from distillation column 12 via line 16 to reactor 20. The $C_6$ cut is mixed with hydrogen stream 56 prior to entering reactor 20. The molar ratio of hydrogen to hydrocarbon in the mixed feed can range from about 5/1 to 0.01/1. Reactor 20 contains a high activity, noble metal containing ring opening catalyst. Reactor 20 pressure can range from 50–1500 psig, preferably about 450 psig. $C_6+$ feed rates can vary from about 0.1 to 10 LHSV. The low octane paraffins and cycloparaffins in the $C_6$ cut are partially converted to isoparaffins in Reactor 20. The effluent from Reactor 20 passes through heat exchanger 22 via line 24, and into an isomerization reactor 40 via line 25.

Reactor 40 contains an amorphous, chlorided alumina catalyst. Reactor 40 pressure can range from 50–1500 psig, preferably about 435 psig. Feed rates can vary from about 0.1 to 10 LHSV. A small amount of organic chloride (10–500 ppm Cl on total feed) is injected into the feed prior to reactor 40. Organic chlorides, such as carbon tetrachloride, are needed to maintain isomerization activity of chlorided alumina catalysts. The total effluent from reactor 40 is passed to liquid-gas separator 50 via line 42. Gas in the separator is mixed with makeup hydrogen from line 52 and recycled via line 55 through compressor 54 and line 56 to reactor 20. Recycle gas is a mixture of $C_4$-hydrocarbons, hydrogen and chloride promoter.

$C_6$ paraffins and cycloparaffins are partially converted to isoparaffins in Reactor 40. The liquid component in the gas-liquid separator is sent via line 58 to distillation column 60. $C_5+$ hydrocarbons are collected from the bottom of the column and recycled via line 62 to distillation column 12 where high octane isoparaffins are collected overhead in line 14 and used as a high octane blending component. Unconverted $C_6$ paraffins and cycloparaffins are reacted to extinction by recycling through line 16. Normally gaseous compounds which are soluble in the liquid from the gas-liquid separator 50 ($H_2$, chloride promoter, $C_4$-hydrocarbons) are concentrated at the top of distillation of column 60 and piped to a caustic scrubber and/or isobutane recovery facility via line 64.

A $C_5$ paraffin stream may be upgraded with this process. The $C_5$ paraffin stream may enter the process prior to reactor 20 and reactor 40.

Figure 2:
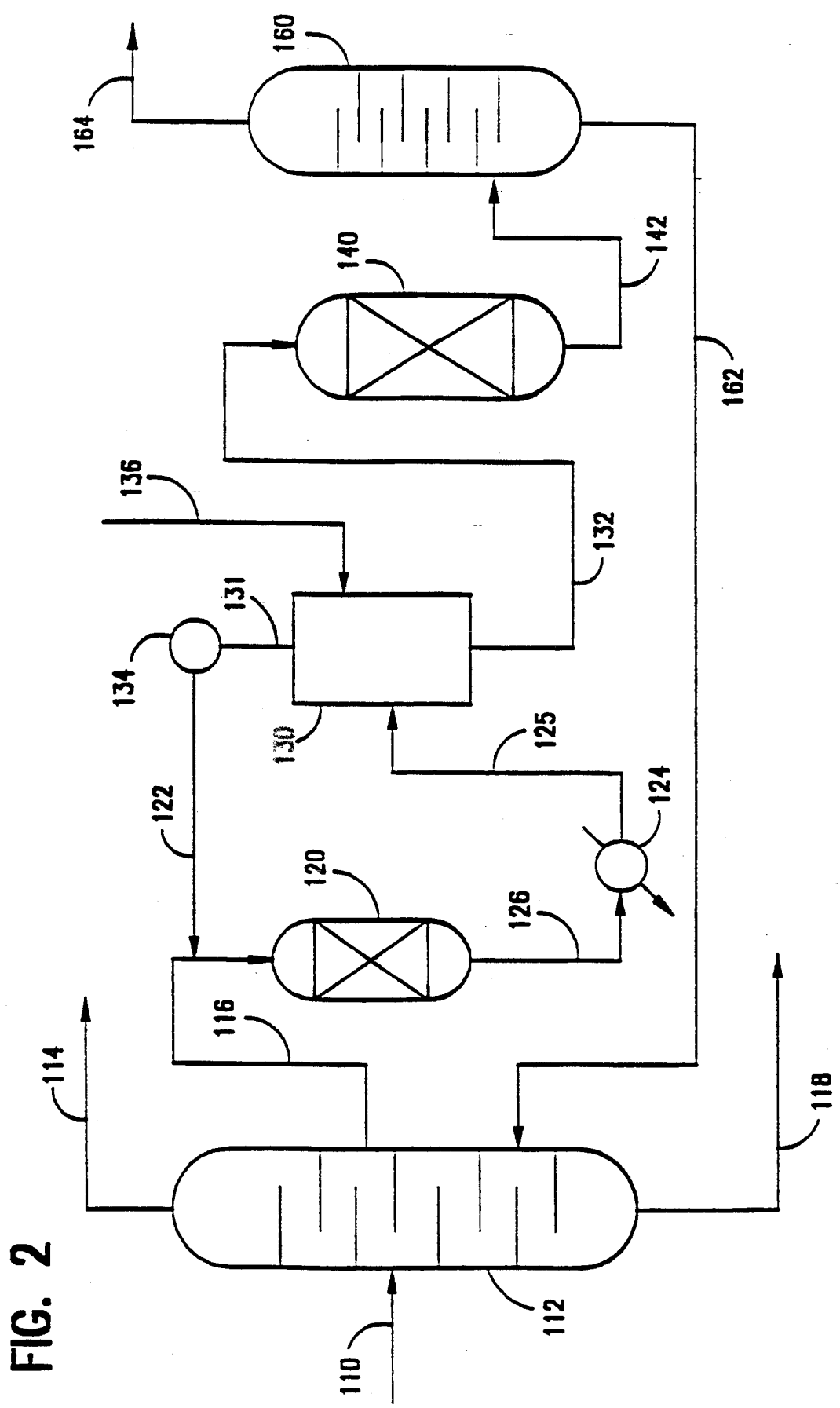

FIG. 2 provides a schematic representation of another embodiment of the present process.

$C_6+$ naphtha enters through line 110 into distillation column 112. The distillation column produces three cuts: a high octane blending fraction termed "isomerate" (primarily 2,2-dimethylbutane and lighter hydrocarbons) which is piped overhead via line 114 to the refinery gasoline pool, a $C_7+$ fraction piped from the bottom through line 118 to the reformer, and a $C_6$ hydrocarbon fraction which passes through line 116 to Reactor 120. The $C_6$ hydrocarbon fraction contains hexane, methylpentanes, 2,3-dimethylbutane, methylcyclopentane and cyclohexane as the predominant components.

The low octane $C_6$ paraffins and cycloparaffins are piped from distillation column 112 via line 116 to Reactor 120. The $C_6$ cut is mixed with hydrogen stream in line 122 prior to entering Reactor 120. The molar ratio of hydrogen to hydrocarbon in the mixed feed can range from about 5/1 to 0.01/1. Reactor 120 contains a high activity, noble metal loaded ring opening catalyst. Reactor 120 pressure can range from 50–1500 psig, preferably about 450 psig. $C_6$ feed rates to Reactor 120 can vary from about 0.1 to 10 LHSV. The low octane paraffins and cycloparaffins in the $C_6$ cut are partially converted to isoparaffins in Reactor 120. The effluent from Reactor 120 passes through heat exchanger 124 from line 126, and into gas-liquid separator 130 via line 125.

The liquid component from gas-liquid separator 130 passes to Reactor 140 via line 132. The feed to Reactor 140 contains only dissolved hydrogen, no make-up hydrogen is added. The gaseous component from gas-liquid separator 130 is recycled via line 131 through compressor 134 and via line 122 to Reactor 120. The recycle gas contains mostly hydrogen with a lesser amount of $C_4$-hydrocarbons. Pure hydrogen can be added to the separator via line 136 to adjust the hydrogen purity in stream 122.

Reactor 140 contains an amorphous, chlorided alumina catalyst. Reactor 140 pressure can range from 50–1500 psig, preferably about 435 psig. Feed rates can vary from about 0.1 to 10 LHSV. A small amount of organic chloride (10–500 ppm Cl on total feed) is injected into the feed prior to Reactor 140. Organic chlorides, such as carbon tetrachloride, are needed to maintain isomerization activity of chlorided alumina catalysts.

$C_6$ paraffins and cycloparaffins are partially converted to isoparaffins in Reactor 140. The total effluent from Reactor 140 passes through line 142 to distillation column 160. $C_5+$ hydrocarbons are collected from the bottom of distillation column 160 and recycled via line 162 to distillation column 112 where high octane isomerate is collected overhead and low octane $C_6$ paraffins and cycloparaffins are reacted to extinction by recycling through line 116. Normally gaseous products which are soluble in the effluent from Reactor 140 ($H_2$, chloride promoter, $C_4$-hydrocarbons) are concentrated at the top of distillation column 160 and piped to a caustic scrubber and/or isobutane recovery facility via line 164.

A $C_5$ paraffin stream may also be upgraded with this process. The $C_5$ paraffin stream may enter the process prior to Reactor 120 or Reactor 140.

EXAMPLE 1

This Example describes the preparation of a tungstate-modified zirconia catalyst. One part by weight of zirconyl chloride, $ZrOCl_2 \cdot 8H_2O$, was added to 3 parts by weight of a 10M $NH_4OH$ solution. The resulting slurry, $Zr(OH)_4$, was filtered and washed with 5 parts of distilled deionized water, then air dried at 140° C. for 8 hours. Approximately 4 parts by weight of the resulting $Zr(OH)_4$ were impregnated via incipient wetness with 1 part of an aqueous solution containing 1 part of ammonium metatungstate, $(NH_4)_6H_6W_{12}O_{40}$. The resulting material was dried for 2 hours at 120° C. and then calcined at 800° C. in flowing air for 2 hours. This material had a calculated mole ratio of $ZrO_2/WO_3$ of 11.6.

Seventy-five parts by weight of this calcined material, referred to hereinafter as $WO_x/ZrO_2$, were impregnated with an aqueous solution containing 1 part of $H_2PtCl_6 \cdot 6H_2O$, dried at 120° C. and then calcined at 350° C. in flowing air for 3 hours The resulting catalyst was reduced in hydrogen at 300° C. before testing. This catalyst is referred to hereinafter as $Pt/WO_x/ZrO_2$.

EXAMPLES 2–4

These Examples describe the effect of chlorine in the catalytic behavior of $Pt/WO_x/ZrO_2$ during ring opening of $C_6$ cyclic hydrocarbons. A simulated commercial feed, having the composition given in Table 1, was charged through a fixed-bed, down-flow reactor containing the $Pt/WO_x/ZrO_2$ catalyst described in Example 1. The reactor effluent of each run was analyzed by gas chromatography to determine product composition. Results and operating conditions are presented in Table 2. Example 2, in Table 2, refers to the results obtained using a chlorine-free feed. Example 3 indicates the results on the chlorine-containing feed experiment which was performed at the same operating conditions as those of Example 2. Comparison of Examples 2 and 3 indicate that the conversion of cyclics increases from 38.1% to 48.6%, while the $C_5+$ product yield decreases from 98% to 95%, upon addition of 700 ppm of chlorine. The chlorine was added to the feed in the form of $CCl_4$. Example 3 shows the results from a chlorine-containing experiment performed at 275° C.

TABLE 1

| FEED COMPOSITION | |
|---|---|
| Component | Wt. % |
| n-Hexane (n-$C_6$) | 50.0 |
| Methylcyclopentane (MCP) | 14.5 |
| Cyclohexane (CH) | 31.7 |
| Benzene (BZ) | 3.9 |

TABLE 2

| Example | 2 | 3 | 4 |
|---|---|---|---|
| Operating Conditions | | | |
| Temperature (°C.) | 260 | 260 | 275 |
| Pressure (psig) | 450 | 450 | 450 |
| LHSV (hr$^{-1}$) | 0.6 | 0.6 | 0.6 |
| $H_2/C_6$-mixture (mol/mol) | 2 | 2 | 2 |
| Chlorine in feed (ppm) | 0 | 700 | 700 |
| Product Composition (wt. %) | | | |
| $C_4-$ | 1.9 | 5.0 | 13.4 |
| i-$C_5$ | 1.1 | 2.7 | 5.6 |
| n-$C_5$ | 0.4 | 0.8 | 1.7 |
| CP | 0.2 | 0.1 | 0.2 |
| 2,2-DMB | 10.1 | 6.1 | 6.3 |
| 2,3-DMB | 5.6 | 6.1 | 5.9 |
| 2MP | 21.5 | 22.4 | 21.5 |
| 3MP | 14.1 | 14.8 | 14.0 |
| n-$C_6$ | 12.3 | 12.8 | 11.7 |
| MCP | 23.7 | 19.6 | 13.2 |
| CH | 7.3 | 6.1 | 3.4 |
| BZ | 0 | 0 | 0 |
| $C_7+$ | 1.8 | 3.7 | 3.0 |
| $C_5+$ Yield (wt. %) | 98.1 | 95.0 | 86.6 |
| Ring Opening Conversion (%) | 38.1 | 48.6 | 66.8 |

Examples 5–14, which follow, demonstrate effects of refluxing hydrated zirconia with an $NH_4OH$ solution prior to contact with a source of tungstate ion.

EXAMPLE 5

This Example describes the preparation of a hydrous $ZrO_2$ support. One part by weight of zirconyl chloride, $ZrOCl_2 \cdot 8H_2O$, was dissolved in 10 parts $H_2O$ and concentrated $NH_4OH_{(aq)}$ added until the solution pH was ~9. The resulting slurry, $Zr(OH)_4$, was filtered and washed with 10 parts of distilled, deionized water. The solid was air dried at 130° C. for 16 hours.

EXAMPLE 6

This Example describes the preparation of a $WO_x/ZrO_2$ catalyst from the zirconia support described in Example 5. Approximately 5.6 parts by weight of the dried product from Example 5 was impregnated via incipient wetness with 4.2 parts of an aqueous solution containing 1 part of ammonium metatungstate, $(NH_4)_6H_6W_{12}O_{40}$. The resulting material was dried in air and then calcined at 825° C. in air for 3 hours.

EXAMPLE 7

This Example describes the preparation and use of a $Pt/WO_x/ZrO_2$ catalyst from the resultant product described in Example 6. To 1 part of an 8% $H_2PtCl_6$ solution was added 2.5 parts of $H_2O$. This mixture was then used to impregnate by incipient wetness 7 parts of the dried product (at 130° C.) from Example 6. The catalyst was then calcined at 300° C. in air for 2 hours. This catalyst was designated Catalyst A. In the catalytic experiments, Catalyst A was reduced with $H_2$ (100 cc/min) at 300° C. and atmospheric pressure for 4 hours. The unit was then brought to the desired conditions and hexane feed introduced. Catalytic data and results are given in Table 3.

EXAMPLE 8

This Example describes the preparation of another $WO_x/ZrO_2$ catalyst using the zirconia support described in Example 5. Approximately 2.4 parts by weight of the dried product from Example 5 was impregnated via incipient wetness with 2.6 parts of an aqueous solution containing 1 part of ammonium metatungstate. The resulting material was dried in air and then calcined at 825° C. in air for 3 hours.

EXAMPLE 9

This Example describes the preparation and use of a $Pt/WO_x/ZrO_2$ catalyst from the resultant product described in Example 8. To 1 part of an 8% $H_2PtCl_6$ solution was added 2.5 parts of $H_2O$. This mixture was then used to impregnate by incipient wetness 7 parts of the dried product (at 130° C.) from Example 8. The catalyst was then calcined at 300° C. in air for 2 hours. This catalyst was designated Catalyst B. In the catalytic experiments, Catalyst B was reduced with $H_2$ (100 cc/min) at 300° and atmospheric pressure for 18 hours. The unit was then brought to the desired conditions and hexane feed introduced. Catalytic data and results are given in Table 4.

EXAMPLE 10

This Example describes the preparation of the base-treated zirconia support. One part by weight of the filtered wet cake from Example 5 was mixed with 10 parts of distilled, deionized water and the pH of the mixture set to pH ~9 with concentrated $NH_4OH_{(aq)}$. This mixture was refluxed for 16 hours, cooled, filtered, and washed with 10 parts of water. The solid was air dried at 130° C. for 16 hours.

EXAMPLE 11

This Example described the preparation of a $WO_x/ZrO_2$ catalyst from the zirconia support described in Example 10. Approximately 5.6 parts by weight of the dried product from Example 10 was impregnated via incipient wetness with 4.2 parts of an aqueous solution containing 1 part of ammonium metatungstate. The resulting material was dried in air and then calcined at 825° C. in air for 3 hours.

EXAMPLE 12

This Example describes the preparation and use of a $Pt/WO_x/ZrO_2$ catalyst from the resultant product in Example 11. To 1 part of an 8% $H_2PtCl_6$ solution was added 2.5 parts of $H_2O$. This mixture was then used to impregnate by incipient wetness 7 parts of the dried product (at 130° C.) from Example 11. The catalyst was then calcined at 300° C. in air for 2 hours. This catalyst was designated Catalyst C. In the catalytic experiments, Catalyst C was reduced with $H_2$ (100 cc/min) at 300° C. and atmospheric pressure for 4 hours. The unit was then brought to the desired conditions and hexane feed introduced. Catalytic data and results are given in Table 5.

EXAMPLE 13

This Example describes the preparation of another $WO_x/ZrO_2$ catalyst using the zirconia support described in Example 10. Approximately 3.4 parts by weight of the dried product from Example 10 was impregnated via incipient wetness with 2.6 parts of an aqueous solution containing 1 part of ammonium metatungstate. The resulting material was dried in air and then calcined at 825° C. in air for 3 hours.

EXAMPLE 14

This Example describes the preparation and use of a $Pt/WO_x/ZrO_2$ catalyst from the resultant product described in Example 13. To 1 part of an 8% $H_2PtCl_6$ solution was added 2.5 parts of $H_2O$. This mixture was then used to impregnate by incipient wetness 7 parts of the dried product (at 130° C.) from Example 13. The catalyst was then calcined at 300° C. in air for 2 hours. This catalyst was designated Catalyst D. In the catalytic experiments, Catalyst D was reduced with $H_2$ (100 cc/min) at 300° C. and atmospheric pressure for 18 hours. The unit was then brought to the desired conditions and hexane feed introduced. Catalytic data and results are given in Table 6.

At comparable $H_2$ reduction times, the catalysts which were treated by heating with base solution (Catalysts C and D) showed improved yields of the isomerized 2,2-dimethylbutane product over the untreated catalysts (Catalysts A and B) at varying temperatures.

TABLE 3

| Catalytic Data for Hexane Isomerization with Catalyst A | | |
| --- | --- | --- |
| Temperature, °C. | 230 | 240 |
| Pressure, psig | 450 | 450 |
| LHSV | 0.6 | 0.6 |
| $H_2$/HC | 1.4/1 | 1.4/1 |
| Hexane conv., wt. % | 70.6 | 77.9 |
| Selectivity, wt. % | | |
| $C_1$—$C_5$ | 0.5 | 0.8 |
| 2,2-dimethylbutane | 7.9 | 11.6 |
| 2,3-dimethylbutane | 11.1 | 12.0 |
| 2-methylpentane | 49.3 | 46.1 |
| 3-methylpentane | 31.2 | 29.5 |
| Yield, wt. % | | |
| 2,2-dimethylbutane | 5.6 | 9.0 |

TABLE 4

| Catalytic Data for Hexane Isomerization with Catalyst B | | | | |
| --- | --- | --- | --- | --- |
| Temperature, °C. | 200 | 210 | 220 | 230 |
| Pressure, psig | 450 | 450 | 450 | 450 |
| LHSV | 0.6 | 0.6 | 0.6 | 0.6 |
| $H_2$/HC | 1.4/1 | 1.4/1 | 1.4/1 | 1.4/1 |
| Hexane conv., wt. % | 80.5 | 82.0 | 82.9 | 84.0 |
| Selectivity, wt. % | | | | |
| $C_1$—$C_5$ | 0.4 | 1.2 | 2.0 | 2.8 |
| 2,2-dimethylbutane | 12.6 | 14.8 | 19.9 | 21.8 |
| 2,3-dimethylbutane | 13.0 | 12.6 | 11.8 | 11.6 |
| 2-methylpentane | 45.8 | 43.6 | 40.4 | 37.8 |
| 3-methylpentane | 28.2 | 27.8 | 25.9 | 23.9 |
| Yield, wt. % | | | | |
| 2,2-dimethylbutane | 10.1 | 12.1 | 16.5 | 18.4 |

TABLE 5

| Catalytic Data for Hexane Isomerization with Catalyst C | | |
| --- | --- | --- |
| Temperature, °C. | 230 | 240 |
| Pressure, psig | 450 | 450 |
| LHSV | 0.6 | 0.6 |
| $H_2$/HC | 1.4/1 | 1.4/1 |
| Hexane conv., wt. % | 80.4 | 81.7 |

TABLE 5-continued

Catalytic Data for Hexane Isomerization with Catalyst C

| Selectivity, wt. % | | |
|---|---|---|
| $C_1$—$C_5$ | 0.5 | 1.4 |
| 2,2-dimethylbutane | 14.7 | 19.0 |
| 2,3-dimethylbutane | 12.2 | 11.8 |
| 2-methylpentane | 44.1 | 40.9 |
| 3-methylpentane | 28.5 | 26.9 |
| Yield, wt. % | | |
| 2,2-dimethylbutane | 11.9 | 15.5 |

TABLE 6

Catalytic Data for Hexane Isomerization with Catalyst D

| Temperature, °C. | 200 | 210 | 220 | 230 |
|---|---|---|---|---|
| Pressure, psig | 450 | 450 | 450 | 450 |
| LHSV | 0.6 | 0.6 | 0.6 | 0.6 |
| $H_2$/HC | 1.4/1 | 1.4/1 | 1.4/1 | 1.4/1 |
| Hexane conv., wt. % | 81.9 | 82.1 | 83.4 | 84.3 |
| Selectivity, wt. % | | | | |
| $C_1$—$C_5$ | 0.9 | 1.1 | 2.5 | 6.5 |
| 2,2-dimethylbutane | 18.3 | 18.1 | 22.5 | 23.4 |
| 2,3-dimethylbutane | 12.3 | 12.3 | 11.4 | 10.6 |
| 2-methylpentane | 41.7 | 41.6 | 38.6 | 36.2 |
| 3-methylpentane | 26.7 | 26.9 | 25.0 | 23.3 |
| Yield, wt. % | | | | |
| 2,2-dimethylbutane | 15.0 | 14.8 | 18.8 | 19.7 |

Examples 15–27, which follow, demonstrate effects of various conditions for reducing catalysts with hydrogen.

EXAMPLE 15

This Example describes the preparation of a hydrous zirconia support. One part by weight of zirconyl chloride, $ZrOCl_2.8H_2O$, was dissolved in 10 parts $H_2O$ and concentrated $NH_4OH_{(aq)}$ added until the solution pH was ~9. The resulting slurry, $Zr(OH)_4$, was filtered and washed with 10 parts of distilled, deionized water. The solid was mixed with 10 parts of distilled, deionized water, and the pH of the mixture set to pH ~9 with $NH_4OH_{(aq)}$. This mixture was refluxed for 16 hours, cooled, filtered, and washed with 10 parts of water. The solid was air dried at 130° C. for 16 hours.

EXAMPLE 16

This Example describes the preparation of a $WO_x$-/$ZrO_2$ catalyst from the zirconia support described in Example 15. Approximately 3.3 parts by weight of the dried product from Example 15 was impregnated via incipient wetness with 2.6 parts of an aqueous solution containing 1 part of ammonium metatungstate. The resulting material was dried in air and then calcined at 825° C. in air for 3 hours. The resultant product was designated Catalyst E.

EXAMPLE 17

Catalyst F was prepared analogously to Catalyst E except 1.17 parts of ammonium metatungstate was used.

EXAMPLE 18

Catalyst G was prepared analogously to Catalyst E except 1.67 parts of ammonium metatungstate was used.

EXAMPLES 19–21

After calcining, Catalysts E, F, and G were then impregnated with Pt via incipient wetness using a solution of 2.5 parts $H_2O$ and 1 part 8% $H_2PtCl_6$. The catalysts were air dried and then calcined at 300° C. in air for 2 hours.

EXAMPLES 22 AND 23

Catalyst E from Example 19 was tested for hexane isomerization. In two separate runs, prior to contacting with feed hexane, the fresh catalyst was treated with $H_2$ (100 cc/min) at 300° C. for 4 and 18 hours. Experimental conditions and catalyst results are given in Table 7.

EXAMPLES 24 AND 25

Catalyst F from Example 20 was tested for hexane isomerization analogously to Examples 22 and 23. Experimental conditions and catalytic results are given in Table 8.

EXAMPLES 26 AND 27

Catalyst G from Example 21 was tested for hexane isomerization. In two separate runs, prior to contacting with feed hexane, the fresh catalyst was treated with $H_2$ (100 cc/min) at 300° C. for 4 and 72 hours. Experimental conditions and catalytic results are given in Table 9.

For Catalysts E, F, and G, increased yields of isomerized product at constant temperature were observed with the same catalysts treated with hydrogen for 18 hours instead of 4 hours. For Catalyst G, an additional experiment involving $H_2$ pretreatement for 72 hours was performed. Although hexane isomerization activity was still present after the 72 hour pretreatment, the yield of 2,2-dimethylbutane was significantly lower at constant temperature than the yields obtained after 4 hours of $H_2$ pretreatment.

TABLE 7

Catalytic Data for Hexane Isomerization with Catalyst E

| | 4 hours | | 18 hours | | | |
|---|---|---|---|---|---|---|
| Temperature, °C. | 200 | 220 | 200 | 210 | 220 | 230 |
| Pressure, psig | 450 | 450 | 450 | 450 | 450 | 450 |
| LHSV | 0.6 | 0.6 | 0.6 | 0.6 | 0.6 | 0.6 |
| $H_2$/HC | 1.4/1 | 1.4/1 | 1.4/1 | 1.4/1 | 1.4/1 | 1.4/1 |
| Hexane conv., wt. % | 75.3 | 82.0 | 80.5 | 82.0 | 82.9 | 84.0 |
| Selectivity, wt. % | | | | | | |
| $C_1$—$C_5$ | 0.2 | 1.6 | 0.4 | 1.2 | 1.8 | 4.8 |
| 2,2-dimethylbutane | 8.4 | 16.1 | 12.6 | 14.8 | 19.9 | 21.8 |
| 2,3-dimethylbutane | 13.1 | 12.3 | 13.0 | 12.6 | 11.8 | 11.6 |
| 2-methylpentane | 47.8 | 42.4 | 45.7 | 43.5 | 40.5 | 37.9 |
| 3-methylpentane | 30.5 | 27.6 | 28.1 | 27.7 | 26.0 | 23.9 |
| Yield, wt. % | | | | | | |
| 2,2-dimethylbutane | 6.3 | 13.2 | 10.1 | 12.1 | 16.5 | 18.4 |

TABLE 8

Catalytic Data for Hexane Isomerization with Catalyst F

| | 4 hours | | | 18 hours | | |
|---|---|---|---|---|---|---|
| Temperature, °C. | 210 | 220 | 230 | 210 | 220 | 230 |
| Pressure, psig | 450 | 450 | 450 | 450 | 450 | 450 |
| LHSV | 0.6 | 0.6 | 0.6 | 0.6 | 0.6 | 0.6 |
| $H_2$/HC | 1.4/1 | 1.4/1 | 1.4/1 | 1.4/1 | 1.4/1 | 1.4/1 |
| Hexane conv., wt. % | 81.6 | 82.7 | 83.6 | 82.1 | 83.4 | 84.3 |
| Selectivity, wt. % | | | | | | |
| $C_1$—$C_5$ | 0.4 | 0.9 | 2.5 | 1.1 | 2.5 | 6.5 |
| 2,2-dimethylbutane | 9.5 | 17.4 | 21.6 | 18.1 | 22.5 | 23.4 |
| 2,3-dimethylbutane | 12.5 | 12.2 | 11.3 | 12.3 | 11.4 | 10.6 |
| 2-methylpentane | 47.4 | 42.2 | 39.3 | 41.6 | 38.6 | 36.2 |
| 3-methylpentane | 30.2 | 27.3 | 25.4 | 26.9 | 25.0 | 23.3 |

TABLE 8-continued

| Catalytic Data for Hexane Isomerization with Catalyst F | | | | | | |
|---|---|---|---|---|---|---|
| | 4 hours | | | 18 hours | | |
| Yield, wt. % | | | | | | |
| 2,2-dimethylbutane | 6.8 | 14.2 | 17.9 | 14.8 | 18.8 | 19.7 |

TABLE 9

| Catalytic Data for Hexane Isomerization with Catalyst G | | | | |
|---|---|---|---|---|
| | 4 hours | | 72 hours | |
| Temperature, °C. | 200 | 220 | 200 | 220 |
| Pressure, psig | 450 | 450 | 450 | 450 |
| LHSV | 0.6 | 0.6 | 0.6 | 0.6 |
| $H_2$/HC | 1.4/1 | 1.4/1 | 1.4/1 | 1.4/1 |
| Hexane conv., wt. % | 79.8 | 84.5 | 48.9 | 76.7 |
| Selectivity, wt. % | | | | |
| $C_1$–$C_5$ | 0.5 | 3.1 | 0.0 | 0.4 |
| 2,2-dimethylbutane | 14.5 | 25.1 | 2.6 | 10.9 |
| 2,3-dimethylbutane | 21.0 | 11.3 | 11.1 | 12.7 |
| 2-methylpentane | 36.6 | 37.3 | 52.9 | 46.1 |
| 3-methylpentane | 27.4 | 23.3 | 33.4 | 29.9 |
| Yield, wt. % | | | | |
| 2,2-dimethylbutane | 11.6 | 21.3 | 1.3 | 8.44 |

What is claimed is:

1. A process for ring opening and isomerization of hydrocarbons, said process comprising the steps of:
   (a) charging hydrocarbons comprising $C_6$ cyclic hydrocarbons along with a source of chlorine and hydrogen to a first reaction zone, wherein said hydrocarbons and said source of chlorine and hydrogen are contacted with a ring opening catalyst under conditions sufficient to open cyclic hydrocarbons contained in said hydrocarbons, wherein said catalyst comprises (i) a hydrogenation/dehydrogenation component and (ii) an acidic solid component comprising a Group IVB metal oxide modified with an oxyanion of a Group VIB metal; and
   (b) charging a feedstock comprising the hydrocarbon product from said first reaction zone, a source of chlorine and hydrogen to a second reaction zone, wherein said feedstock is contacted with an isomerization catalyst under conditions sufficient to isomerize paraffins.

2. A process according to claim 1, wherein the reaction conditions in the first reaction zone include a temperature of at least 150° C., a pressure of from 50 to 1500 psig and a weight hourly space velocity of from 0.1 to 50 $hr^{-1}$.

3. A process according to claim 2, wherein the reaction conditions in the second reaction zone include a temperature of from about 40° to 180° C., a pressure of from 50 to 1500 psig and a weight hourly space velocity of from 0.1 to 50 $hr^{-1}$.

4. A process according to claim 1, wherein at least 10 wt % of the cyclic hydrocarbon rings charged into said first reaction zone are opened in step (a).

5. A process according to claim 1, wherein said Group IVB metal is zirconium and said Group VIB metal is tungsten.

6. A process for ring opening and isomerization of hydrocarbons, said process comprising the steps of:
   (a) passing hydrocarbons comprising $C_6$ cyclic hydrocarbons and a hydrocarbon recycle stream to a fractionation zone;
   (b) withdrawing a sidecut comprising $C_6$ hydrocarbons and a majority of the $C_6$ cyclic hydrocarbons entering said fractionation zone;
   (c) charging said sidecut along with hydrogen and a source of chlorine to a first reaction zone, wherein said sidecut and hydrogen are contacted with a ring opening catalyst under conditions sufficient to open cyclic hydrocarbons contained in the sidecut, wherein said catalyst comprises (i) a hydrogenation/dehydrogenation component and (ii) an acidic solid component comprising a Group IVB metal oxide modified with an oxyanion of a Group VIB metal;
   (d) charging a feedstock comprising the hydrocarbon product from said first reaction zone, a source of chlorine and hydrogen to a second reaction zone, wherein said feedstock is contacted with an isomerization catalyst under conditions sufficient to isomerize paraffins;
   (e) recovering an effluent from said second reaction zone and returning said effluent to said fractionation zone as said hydrocarbon recycle stream;
   (f) recovering a second stream from said fractionation zone comprising $C_7$ hydrocarbons; and
   (g) recovering a third stream from said fractionation zone comprising 2,2-dimethylbutane and lower boiling hydrocarbons.

7. A process according to claim 6, wherein said catalyst in the first reaction zone and the catalyst in the second reaction zone each comprise platinum.

8. A process according to claim 6, wherein $C_5$ hydrocarbons are cofed into the reaction zone of step (c).

9. A process according to claim 6, wherein at least 25 wt. % of the cyclic hydrocarbon rings charged into said first reaction zone are opened in step (c).

10. A process according to claim 6, wherein said Group IVB metal is zirconium and said Group VIB metal is tungsten.

11. A process for ring opening and isomerization of hydrocarbons, said process comprising the steps of:
   (a) passing hydrocarbons comprising $C_6$ cyclic hydrocarbons and a hydrocarbon recycle stream to a fractionation zone;
   (b) withdrawing a sidecut comprising $C_6$ hydrocarbons and a majority of the $C_6$ cyclic hydrocarbons entering said fractionation zone;
   (c) charging said sidecut along with hydrogen and a source of chlorine to a first reaction zone, wherein said sidecut and hydrogen are contacted with a ring opening catalyst under conditions sufficient to open cyclic hydrocarbons contained in the sidecut, wherein said catalyst comprises (i) a hydrogenation/dehydrogenation component and (ii) an acidic solid component comprising a Group IVB metal oxide modified with an oxyanion of a Group VIB metal;
   (d) removing hydrogen from the effluent of the first reaction zone under conditions so that the effluent has a hydrogen to hydrocarbon mole ratio of less than 0.05;
   (e) recycling hydrogen removed in accordance with step (d) to said first reaction zone;
   (f) charging a feedstock comprising a source of chlorine and the effluent from step (d) having a hydrogen to hydrocarbon mole ratio of less than 0.05 to a second reaction zone, wherein said feedstock is contacted with an isomerization catalyst under conditions sufficient to isomerize paraffins;

(g) recovering an effluent from the second reaction zone and returning said effluent from the second reaction zone to said fractionation zone as said hydrocarbon recycle stream;

(h) recovering a second stream from said fractionation zone comprising $C_7$ hydrocarbons; and (i) recovering a third stream from said fractionation zone comprising 2,2-dimethylbutane and lower boiling hydrocarbons.

12. A process according to claim 11, wherein the catalyst in the second reaction zone comprises alumina, from 0.1 to 1.0 wt. % platinum, and from 2 to 20 wt % of a chloride component.

13. A process according to claim 12, wherein a chloride concentration of from 30 to 300 ppm is maintained in said second reaction zone.

14. A process according to claim 11, wherein at least 50 wt. % of the cyclic hydrocarbon rings charged into said first reaction zone are opened in step (c).

15. A process according to claim 11, wherein said Group IVB metal is zirconium and said Group VIB metal is tungsten.

* * * * *